United States Patent
Klaveness et al.

(10) Patent No.: US 6,610,547 B1
(45) Date of Patent: Aug. 26, 2003

(54) SELECTION OF CONTRAST AGENT DRUG FROM A COMBINATORIAL LIBRARY

(75) Inventors: Jo Klaveness, Oslo (NO); Harald Dugstad, Oslo (NO); Julian Cockbain, London (GB)

(73) Assignee: Amersham Health AS, Olso (NO)

( * ) Notice: Subject to any disclaimer, the term of this patent is extended or adjusted under 35 U.S.C. 154(b) by 0 days.

(21) Appl. No.: 09/705,906

(22) Filed: Nov. 6, 2000

Related U.S. Application Data

(63) Continuation of application No. PCT/GB99/01448, filed on May 7, 1999.

(30) Foreign Application Priority Data

May 7, 1998 (GB) ............................................. 9809776

(51) Int. Cl.$^7$ ...................... G01N 33/566; A61K 49/00; A61K 49/04; A61B 5/055; A61B 8/00
(52) U.S. Cl. .................. 436/501; 435/7.1; 435/DIG. 9; 435/DIG. 19; 435/DIG. 21; 424/9.1; 424/9.2; 424/9.3; 424/9.4; 424/9.52
(58) Field of Search ............................... 424/9.52, 9.36, 424/9.1, 9.2, 9.3, 9.4; 436/501; 435/7.1, DIG. 19, DIG. 14, DIG. 21

(56) References Cited

U.S. PATENT DOCUMENTS 6,045,775 A * 4/2000 Ericcson et al. ............ 424/9.36
6,123,923 A * 9/2000 Unger et al. ................ 424/9.52

FOREIGN PATENT DOCUMENTS

| WO | WO 97 22617 A | 6/1997 |
| WO | WO 97 41856 A | 11/1997 |
| WO | WO 98 10286 A | 3/1998 |
| WO | WO 99 09416 A | 2/1999 |
| WO | WO 99 27133 A | 6/1999 |

OTHER PUBLICATIONS

Konings D.A.M., "Strategies for rapid deconvolution of combinatorial libraries: comparative evaluation using a model system", J Med. Chem, 1997, XP00217709.
Boutin J.A., "Physico–chemical and biological analysis of true combinatorial libraries", Journal of Chromatography B, 1999, XP002117711.
Furka A. et al., "Combinatorial libraries by portioning and mixing", Combinatorial Chemistry & High Throughput Screening, 1999, XP002117712.
Schriemer D.C. et al., "Deconvolution approaches in screening compound mixtures", Combinatorial Chemistry & High Throughput Screening, 1998, XP002117713.

* cited by examiner

*Primary Examiner*—Andrew Wang
*Assistant Examiner*—Tomas Friend
(74) *Attorney, Agent, or Firm*—Bacon & Thomas

(57) ABSTRACT

The invention provides a method of contrast agent drug candidate selection which involves: (i) obtaining a combinatorial library comprising an admixture of potential contrast agent drug candidates each incorporating a reporter moiety which is detectable in the animate human or non-human animal body (e.g. mammalian, avian or reptilian body), said library comprising a plurality of said reporter moieties which are interdistinguishably detectable in said body; (ii) administering said library to an animate human or non-human animal body; (iii) identifying in vivo one or more of said reporter moieties which has a desired distribution and/or elimination pattern in said body and thereby identifying a member of said library which has said pattern site or a sub-set of said library which contains a member of said library which has said pattern.

19 Claims, 1 Drawing Sheet

SELECTION OF CONTRAST AGENT DRUG FROM A COMBINATORIAL LIBRARY

Figure 1:
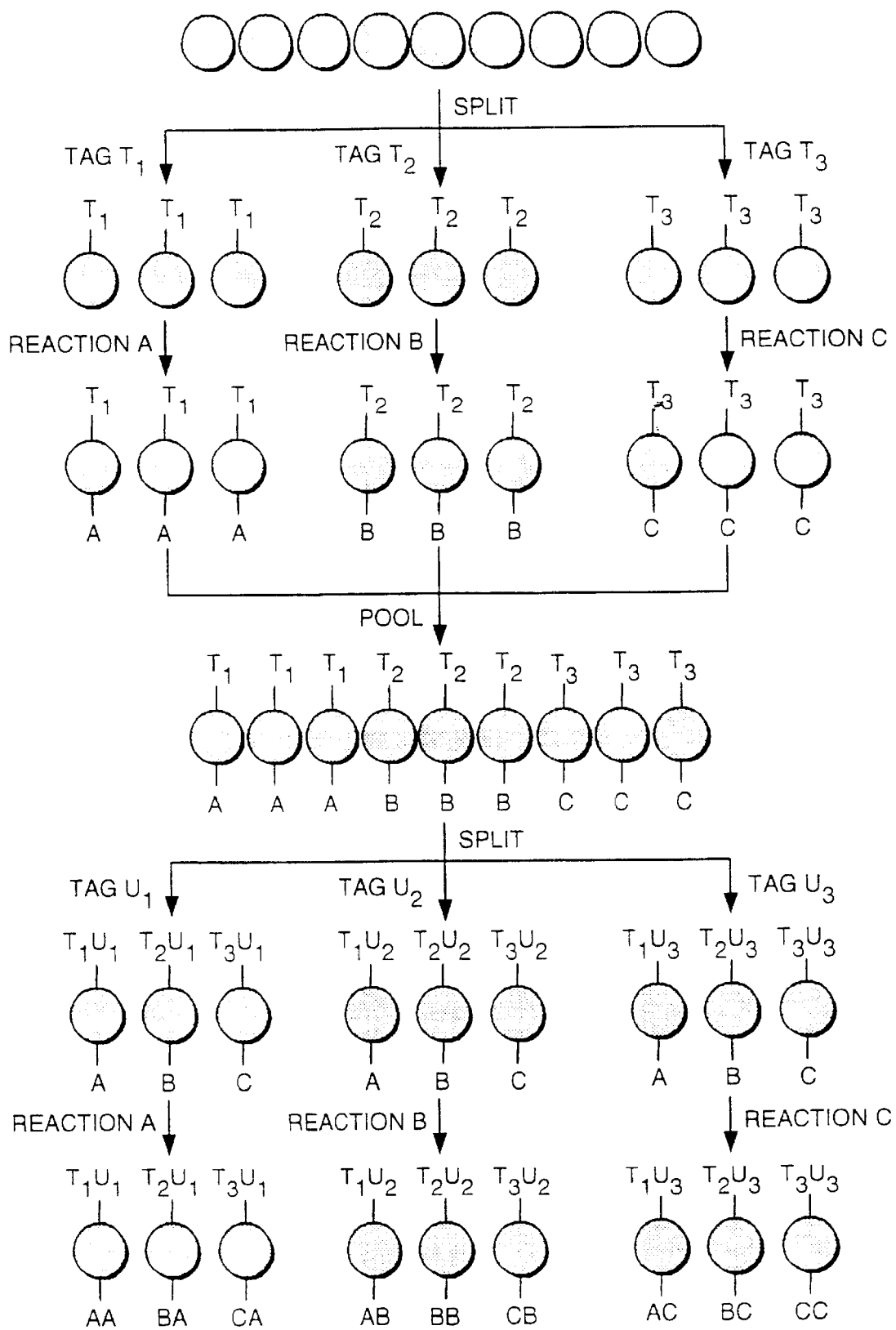

This application is a continuation of International Application PCT/GB99/01448, filed May 7, 1999, of which the entire disclosure of the pending, prior application is hereby incorporated by reference.

This is invention relates to a method of identifying candidate contrast agents ("contrast agent drug candidates") using combinatorial libraries of compounds or molecular aggregates.

Traditionally, drug discovery has involved the manufacture and testing of individual compounds, often as a result of an initial fortuitous finding of efficacy for a naturally occurring compound and the subsequent synthesis of structurally similar compounds. Recently however an alternative approach to drug discovery has developed in which a large range of compounds of random or directed random structure are synthesised and tested for efficacy. In such "combinatorial" libraries, the library members may either be separate or be present in admixture. The present invention is concerned with the latter case.

Such admixture libraries may readily be tested for efficacy in vitro—however if the desired drug effect is found, drug candidate identification requires deconvolution, the identification of which member or members of the library have the desired effect. Several deconvolution techniques have been developed and particular mention here may be made of biological tagging and orthogonal scanning. In biological tagging, the individual library members carry a unique biological tag that can be amplified, e.g. an oligonucleotide sequence or a virus, so enabling the "successful" library member, once isolated from the unsuccessful members, to be identified. In orthogonal scanning, numbers of sub-libraries are screened in order to identify the "successful" library members.

Screening of combinatorial libraries containing the library members in admixture is generally done on an in vitro basis with in vivo testing being left until potential drug candidates have been identified and then being performed using individual drug candidates, much as in conventional drug discovery.

In vitro screening however is of limited applicability since it requires a sample of the target tissue or a culture of target cells to be used and thus it does not allow one to determine whether or not the "successful" library members associate specifically with the target and it does not allow one to determine targeting ability for unknown targets.

It is possible to screen mixed combinatorial libraries in vivo where the library members carry a biological, amplifiable tag. The "successful" library members may then be identified by excision of tissue from the desired target site, amplification and identification. Again however this has drawbacks since the removal of tissue from the animal, and often the sacrifice of the animal, is required and thus this technique is generally suitable only for small laboratory animals such as mice, guinea pigs and rats. Accordingly, it does not generally allow one to determine targeting ability and specificity for unknown targets in larger, e.g. more human-like, animals.

These drawbacks however can be overcome by in vivo screening of a mixed combinatorial library in which the library members incorporate reporters which are detectable and interdistinguishable in vivo.

Thus viewed from one aspect the invention provides a method of contrast agent drug candidate selection which involves:

(i) obtaining a combinatorial library comprising an admixture of potential contrast agent drug candidates each incorporating a reporter moiety which is detectable in the animate human or non-human animal body (e.g. mammalian, avian or reptilian body), said library comprising a plurality of said reporter moieties which are interdistinguishably detectable in said body, (ii) administering said library to an animate human or non-human animal body, (iii) identifying in vivo one or more of said reporter moieties having a desired distribution and/or elimination pattern (e.g. which distributes to a particular site in said body) and thereby identifying a member of said library which has said pattern (e.g. which distributes to said site) or a sub-set of said library which contains a member of said library which has said pattern (e.g. which distributes to said site).

For the candidate contrast agents to be deemed "successful", ie. to progress to a further stage of development, they must possess a desired pattern of biodistribution and bioelimination following administration. This may be referred to by the acronym "ADME" standing for administration, distribution, (metabolism) and excretion. The method of the present invention serves to identify members of the combinatorial library or subsets within the combinatorial library that have an ADME pattern which meets the selection criteria set down for contrast agent candidate identification.

The library members in the combinatorial library used according to the invention incorporate a reporter moiety which is detectable in an animate body. By this it is meant that the reporter should be such as to allow its detection without requiring removal (ie. separation) from the body of a sample of a body site of interest and so also without requiring the animal to be sacrificed. Examples of reporter moieties detectable directly in this fashion include chromophores, heavy atoms, radiolabels and magnetic particles, ie. moieties such as are commonly used for image contrast enhancement in diagnostic imaging modalities such as light imaging, X-ray imaging, magnetic resonance imaging, ultrasound imaging and nuclear imaging.

However it is central to the invention that the library should contain a plurality of interdistinguishable reporters, ie. reporters which can not only be detected in the animate body but which can be distinguished from each other in such detection. Particularly desirably, each different library member has a different reporter so that detection of a reporter identifies the library member it forms part of. In this case the number of different reporters is equal to the number of different library members. However in practice it will often be preferable to have a smaller number of different reporters than different library members so that detection of a reporter identifies a sub-set of the library members that include that particular reporter. In this case, with the sub-set identified, orthogonal scanning techniques can be used to identify the "successful" members of the initial library. Conventional deconvolution techniques may be used in this regard. Thus for example a series of libraries may be scanned in which the reporters used to tag the library members are varied with the successful members being identified by a unique combination of reporters detected in the series of scans. Alternatively a sub-library may be prepared using the members of the initially identified library sub-set but labelling these with a plurality of different reporters. A second scan can then be used to identify either the successful library member or a smaller sub-set containing it (in which latter case the procedure is repeated to identify the successful library member).

The interdistinguishability of the reporters may be achieved in a variety of ways. Thus for example reporters may be used which are detectable by different imaging techniques (in which case screening will involve imaging the body or a site of interest therein using two or more imaging techniques) or alternatively or additionally reporters may be used which are interdistinguishable in one imaging technique. In this regard, particular mention may be made of radiolabels which emit detectable radiation of different types or energies detectable by multichannel gamma counters, of chromophores with different characteristic absorption or emission maxima, of tags with different detectable radiofrequencies (see for example Nicolaou et al. Angew. Chem. Int. Ed. Engl. 34: 2289–2291 (1995)), of tags with different magnetic moments (preferably using different monosized crystals, optionally differentiating with SQUID magnetometers, or Mössbauer or other spectroscopie techniques), of tags with different paramagnetic centres (e.g. differentiating using epr), or tags with differently sized or membraned gas containing microballoons. In a further embodiment of the invention a combination of reporters which may be interdistinguishable in one or more imaging techniques may be incorporated in individual members of the combinatorial libraries.

For ease of operation, it will be preferred that the reporters used be detectable in a single imaging modality, or less preferably up to 5 imaging modalities.

Direct means of contrast agent direction may involve a combination of detection techniques, e.g. HPLC-MS, MS-MS, capillary electrolysis-mass spectroscopy (CE-MS), HPLC-NMR, etc.

In order to avoid the situation where differences in targeting ability of the library members may not be determinable due to the differences in modification of targeting ability caused by different chemical or physical properties of the different reporter tags used, it may be desirable to use only chemically/sterically similar reporters in each library. Thus for example the reporters used in a library might all be phthalocyanines, with each different reporter having a characteristic absorption or emission maximum.

The reporter species mentioned above are all directly detectable. However in the present invention it is also possible to use indirectly detectable reporters, for example materials which become detectable or produce a detectable material through interaction with a further material or materials which modify the detectability of a further material. Thus for example a reporter might be a specific binding partner (e.g. an oligopeptide or oligonucleotide) for a component of a detectable material (e.g. a contrast agent comprising a magnetic particle or a gas containing vesicle) which could be administered after the library has been administered and after unsuccessful library members have been cleared from the site of interest. Since a vast number of complimentary binding partners may be produced relatively easily and since the library members do not need to contain a directly detectable moiety which might adversely affect their biodistribution, this embodiment offers a simple solution to the production of a deconvolutable library usable in vivo without requiring animal sacrifice.

The method of the present invention will generally involve the use of at least one combinatorial library having at least 3 library members, preferably at least 10, more preferably at least 50 members and still more preferably at least 100 members. In certain cases the libraries used may contain significantly larger numbers of members, e.g. up to $10^4$ or even up to $10^6$. The smaller the number of library members the more important it will be to use rational rather than entirely random design of the library members in order to have a reasonable expectation of finding a "successful" member of the library. The concentration of each library member in the library likewise will depend upon the detectability of the reporters used as well as upon the means of administration and whether or not a target site of interest has already been identified. In general however, as in most combinatorial chemistry library screens, it will be desirable for the library used to contain multiple copies of the library members.

The number of different, interdistinguishable reporters present in the library will also depend upon a number of factors. Thus while ideally each library member is uniquely tagged, in certain cases the nature of the selected reporter moieties may not permit unique tagging of the members of a relatively large library. While there will be at least two different reporters, preferably there will be at least 5, more preferably at least 10 and especially preferably at least 25. Put otherwise, the ratio of library members to different reporters will ideally be 1:1 but may be as low as 10000:1 with ratios in the range 1:1 to 11000, 1:1 to 1:200, more especially 1:1 to 1:50 and even more especially 1:1 to 1:25 being acceptable.

Where library members are not uniquely tagged, deconvolution techniques may be used as mentioned above to identify the successful library member(s) or at least to identify a smaller library sub-set in which the successful library member may be found. If a small enough sub-set is identified then the final identification of the successful library member need not involve further deconvolution but might instead involve individual testing of members of that sub-set and if desired may involve removal of samples and if required animal sacrifice.

Identification of successful library members may be sufficient to allow selection of a drug candidate. However, especially where library members have been generated on a random basis, identification of successful and unsuccessful members may permit the generation of further libraries with an increased expectation of containing successful members. Thus for example where the library members are oligomers or are framework decorated monomers produced by reaction of differently substituted precursor molecules (e.g. amino acid or nucleotide monomers or the "jigsaw piece" reagents used to construct a framework decorated monomer), then monomers, monomer strings or jigsaw piece reagents which occur in unsuccessful but not successful library members may be excluded and further analogs of monomers, monomer strings or jigsaw piece reagents which occur in successful but not unsuccessful library members may be added in the synthesis of the subsequent library. Typically, iterative library redesign might be carried out up to 10 or even more times in order eventually to reach a drug candidate suitable for selection.

The method of the invention may thus involve screening of a plurality of libraries, e.g. 2 to 20, preferably 2 to 10, with successive libraries being designed on the basis of the results from the earlier libraries and iteration being stopped when one or more conjugates having suitable properties are found.

As mentioned above, the reporters used need not be directly detectable. It is also not essential that they be detectable (directly or indirectly) at the site within the body at which they accumulate. Thus for example the body can be used to separate successful from unsuccessful library members with the successful members (or subsets) being identified by elimination by identification of the unsuccessful members (or subsets) or on release from their accumulation site, for example by administration of a ligand for that site.

In effect this means that the animal body is used as a means for chromatographic separation, e.g. affinity chromatographic separation, of the library members.

In this aspect of the invention, it is not necessary that the reporter be detectable within the animate body as the detection may be effected using a fluid sample from the body (e.g. a blood, urine, CSF, bile, etc. sample) which can be taken for analysis without requiring the animal to be damaged or sacrificed. Since a fluid sample may be taken for analysis, it is especially preferable that, where the fluid sample is one expected to contain a successful library member, the reporter used be one which is capable of amplification, e.g. an oligonucleotide or an organism (for example a phage), and that the library members be uniquely tagged.

Thus viewed from a further aspect the invention provides a method of contrast agent drug candidate selection which involves:

(i) obtaining a combinatorial library comprising an admixture of potential contrast agent drug candidates each incorporating a detectable reporter moiety, said library comprising a plurality of said resorter moieties which are interdistinguishably detectable, (ii) administering said library to an animate human or non-human animal body, (iii) preferably without sacrificing said animal, obtaining body fluid from said body and identifying one or more of said reporter moieties present or not present in said body fluid and thereby identifying a member of said library or a subset of said library which contains a member of said library which is present or not present in said body fluid.

In this method, step (iii) may if desired be effected repeatedly or continuously in order to determine the time dependence of the appearance in the obtained body fluid of the library members or subsets. For certain body fluids, such as blood or CSF, the obtained fluid may be continuously returned to the body after analysis, ie. analysis may be performed ex vivo.

In this method of the invention, after the library has been administered and after sufficient time has elapsed for a separation of successful and unsuccessful library members to have occurred in the body, a material which binds to a site of interest (e.g. a cell surface receptor) may be administered so as to displace successful library members which have bound to that site whereafter such displaced successful library members may be detected in the body fluid in question, e.g. blood or urine.

The methods of the invention are applicable to library screening in vivo using an animate animal subject. However they may also be carried out using isolated but living organs, for example the heart. This aspect of the invention is particularly applicable where the reporters used are difficult to detect with the desired spatial discrimination in the live animal or where the intention is to identify materials whose ability to accumulate at particular sites of interest is or is not affected by abnormal functioning of the particular organ.

In the methods of the invention, the manner in which the reporters are detected will depend upon the nature of the reporters.

Where the reporter is an entity detectable directly or indirectly in an imaging modality, then that modality may be used with images being generated of the whole animal or a region of interest therein or of a body fluid obtained therefrom. Whole body imaging is particularly desirable as it enables identification of library members which distribute to body sites not previously identified as potential targets and also enables identification of the specificity of the library members' distribution. Thus where, for example, the target site of interest is the heart and two library members accumulate there, the preferred candidate may be the one with lesser accumulation in other tissues. Whole body imaging is feasible with many imaging techniques such as mr, X-ray (e.g. CT) and nuclear imaging.

Where the reporter is difficult to detect at a distance, or where the location is difficult to determine when there are significant amounts of tissue between reporter and detector, as is for example the case with light imaging techniques, it may be preferred to image only a region of interest within the body and even to insert the detector into the body through natural or surgically created apertures so as to ensure adequate proximity of detector and region of interest. Alternatively it may be desirable surgically to expose tissues or organs of interest, e.g. by removing skin, by opening the abdominal cavity or by removing part of the cranium.

Where the library members are to be detected in a body fluid, samples of this may be removed from the body and analysed, or blood may be continuously taken from the body, analysed and returned. In general, analysis of body fluids may be simpler than whole body or region of interest imaging as the fluids may be treated before analysis, e.g. to concentrate the reporter, to amplify the reporter, to remove non-reporter components (such as erythrocytes), etc. As a result, reporters which would not be detectable in vivo (e.g. since their identification requires amplification and sequencing or since their concentrations in vivo are too low or since their detection requires modification or destruction of their chemical environment or removal of surrounding tissue) may be used. Particularly preferably, the reporters used, where detection is by analysis of a body fluid, will be amplifiable reporters such as oligonucleotide "tags".

The method of the invention may be used to identify a drug candidate (optionally incorporating a reporter moiety) or a component, e.g. a targeting vector, for a drug candidate (again optionally incorporating a reporter moiety). Where a component is identified, the drug candidate will comprise this component bound to or otherwise associated with at least one further component, such as for example a therapeutically or diagnostically effective moiety which may be targeted to a desired body site by the identified component. Where the drug candidate is to comprise a reporter moiety, this may or may not be the same as the reporter moiety contained in the corresponding library member and indeed generally will be a reporter moiety detectable in vivo using a diagnostic imaging modality, e.g. in an X-ray (e.g. CT), mri, ultrasound, nuclear imaging (e.g. scintigraphy, PET or SPECT), magnetotomographic or light imaging modality.

In the methods of the invention, the combinatorial library is administered as a mixture of the library members to the living animal or living organ. This will generally involve administration of a solid, powder, syrup, solution, dispersion, suspension, spray, gel, emulsion, capsule or any other convenient dosage form by any convenient dosage route, e.g. parenterally or enterally for example into the nose, lungs, gastrointestinal tract, vagina, bladder, uterus, vasculature or muscles, or topical or subcutaneous administration. In general, administration will preferably be topical, subcutaneous, oral, rectal intramuscular, intraarterial or intravenous.

Where "success" for a library member corresponds to a cross-barrier uptake, e.g. transdermal uptake, uptake from the gut, crossing of the blood brain barrier, etc., the administration route will preferably be direct to one side of the barrier in question, e.g. onto the skin or an exposed mucous membrane, into the gastrointestinal tract or into the vasculature, and detection of "success" will involve detection of library members which have crossed the relevant barrier, e.g. by passing into the blood following topical application or administration into the GI tract or by passing into the CSF following administration into the vasculature. Where "success" corresponds to accumulation in a particular organ or tissue, administration will generally be into the vasculature upstream of that organ or tissue, into the GI tract, to the skin, into muscle, into the lungs or directly into that organ or tissue. Where "success" corresponds to prolonged retention in or minimal uptake from a body duct or cavity (e.g. the vasculature), administration will generally be into that duct or cavity.

It will be apparent therefore that "success" depends upon the desired distribution of or affect of the library member. The contrast agent candidate to the selection of which the invention is directed is a diagnostic agent but in addition it may be a therapeutic or prophylactic drug, e.g. with one or more of the relevant properties being provided by a moiety which will be associated with a candidate component identified by the method of the invention.

Evaluation of "success" in sub-libraries where a previous library has achieved a desired effect may also include monitoring of physiological response (e.g. suppression of infection, anti-tumor activity, blood or other body fluid component analysis, blood pressure, cardiac function, etc) so that library members achieving a desired combination of effects or avoiding undesired effects may be identified.

"Success" may for example represent a desired targeting effect, a desired contrast effect, a desired therapeutic effect, etc. Thus a library member may for example comprise a first reporter moiety effective as a contrast agent in a particular diagnostic imaging modality, a tag unique to the member or a set of members and, optionally, a targeting moiety. In this instance "success" may be indicated by contrast effectiveness in the selected imaging modality with the tag being used as the means of establishing which reporter moiety or reporter/targeting vector combination enjoys this success.

Thus, in one embodiment, the method of the invention may be used to identify a vector moiety which may or may not be essentially physiologically inert in itself but which may be used to target a known effective therapeutic, prophylactic or diagnostic moiety to a body site of interest.

In an alternative embodiment, the methods of the invention may be used to identify contrast agent candidates or components thereof which are capable of detection (ie. may suitably be used as contrast agents in medical diagnostic imaging procedures) and which may have a desired physiological effect, and have the ability to reach a body site where they may exert that physiological effect or be detected. The invention is thus particularly suited for the identification of contrast agents which have a desired effect and are capable of reaching a desired body site from their administration site, e.g. tumor targeting diagnostic agents or combined therapeutic and diagnostic agents.

When one or more contrast agent drug candidates are selected using the methods of the invention, these contrast agent drug candidates, or a component or derivative thereof may be manufactured and if desired formulated with at least one pharmaceutically acceptable carrier or excipient. Such components of contrast agent drug candidates may for example be a targeting vector for the drug candidate. When such a component is identified the drug candidate may comprise this component bound to or otherwise associated with at least one further component, such as for example a therapeutically or diagnostically effective moiety. The term "derivative" as used herein includes a contrast agent drug candidate as identified in the methods of the invention but modified to incorporate a different reporter moiety or targeting vector. The term "derivative" also includes a modified contrast agent drug candidate wherein the reporter moiety is replaced by a therapeutic moiety.

Thus viewed from a further aspect the invention provides a process for the production of a contrast agent drug substance which comprises (i) selecting a contrast agent drug candidate or a component thereof using a selection method comprising a method according to the invention, (ii) optionally selecting a diagnostically or therapeutically effective drug component, (iii) manufacturing said contrast agent drug candidate or a contrast agent drug substance comprising the components selected in steps (i) and (ii), and (iv) optionally formulating the contrast agent drug candidate or contrast agent drug substance manufactured in step (iii) into a pharmaceutical composition together with at least one pharmaceutically tolerable carrier or excipient.

The library members may take a variety of forms thus in particular they may be molecules or molecular aggregates, e.g. vesicles or coated particles and they may or may not contain the oligomeric or decorated framework monomer structures typical of combinatorial chemistry libraries. Particularly preferably, the non-reporter part of the library members will be an oligomeric or decorated framework monomer structure typical of combinatorial chemistry libraries. Especially suitably, the non-reporter part is an oligopeptide, a peptoid, an oligosaccharide, an oligonucleotide or a non-polymeric small organic molecule (e.g. of molecular weight below 1000 D). The preparation of libraries of such materials has been widely described in the literature in the last decade (see for example M. Gallop et al. in J. Med. Chem., 37: 1233–1251 (1994); E. M. Gordon et al. in J. Med.Chem., 37: 1381–1401 (1994); M. C. Pirrung in Chemtracts—Organic Chemistry, 8: 5–12 (1995); W. J. Dower et al in Ann Rep in Med.Chem. 26: 271–280 (1991); W. H. Moos et al in Current Opinions in Structural Biology, 3: 580–584 (1993); M. R. Pavia et al. in Bioreg.Med.Chem. Lett., 3: 381–475 (1995); N. K. Terrett et al. in Tetrahedron, 51: 8135–8173 (1995); S. E. Blondelle et al. in Antimicrobial Agents and Chemotherapy, 40: 1067–1071 (1996); M. C. Desar et al. in Drug Development Research, 33: 174–188 (1994); D. J. Ecker in Biotechnology, 351–360 (1995); D. J. Gravert et al. in TIBTECH, 14: 110–112 (1996); D. Madden et al. in Perspectives in Drug Discovery Today, 1: 248–254 (1996); D. P. Curran in Chemtracts—Organic Chemistry, 9: 75–87 (1996); J. Eicher et al. in Molecular Medicine Today, 174–180 (1996); P. J. Schatz in Current Opinion in Biotechnology, 5: 487–494 (1994); J. Eicher et al. in Medicinal Research Reviews, 15: 481–496 (1995); S. Bormen in Chem. & Eng. News, February 12: 2954 (1996); M. Rinnova et al. in Collect. Czech.Chem. Commun, 61: 171–231 (1996); E. M. Gordon in Acc.Chem. Res., 29: 144–154 (1996); R. Cortese (Ed) in "Combinatorial Libraries, Synthesis, Screening and Application Potential" (Water de Gruyter, 1996); A. M. Thayer in Chem. & Eng. News, February 12: 57–73 (1996); A. Furka et al. in Drug Development Research, 36: 1–12 (1995); M. H. Lyttle in Drug Development Research, 35: 230–236 (1995); A. W. Zarnik in Chemtracts—Organic Chemistry, 8: 13–18 (1995); and X-Willard in Eur. J.Med. Chem., 31: 87–98 (1996).

Such non-reporter components may readily be conjugated to a reporter or tag, e.g. by covalent bonding of a functional group at a terminus or on a side chain, or by conjugation to a moiety which will act as an anchor to the reporter, e.g. a lipophilic group which may associate with the membrane of a vesicle or an ionic group which can bond to the surface of an inorganic particle such as a magnetic metal oxide.

The reporter component may for example comprise a non-metal radioisotope, a metallated chelate complex or an oligopeptide or oligonucleotide covalently bonded to the non-reporter component, an organic chromophore or a particulate (e.g. a vesicle containing gas, a solid contrast agent or a contrast agent solution) to the surface of which is covalently or non-covalently attached the non-reporter component.

The present invention will now be illustrated further by the following non-limiting Examples:

EXAMPLE 1

Library Synthesis

Synthesis of a library of radiopharmaceutical contrast agents comprising an $^{111}$Indium chelate of DO3A conjugated to endothelin related peptides:

A mixture of endothelin related peptides (commercially available from Advanced ChemTech, USA) is added to a solution of 10-[7-(4-isothiocyanatophenyl)-2-hydroxy-5-oxo-1,4,7(carboxymethyl)-1,4,7,10-tetraazacyclododecane (prepared according to Dinkelborg et al. in WO 96/02274, Example 1) in DMF. The mixture is stirred for 48 hours at ambient temperature followed by evaporation of the solvent and labelling with $^{111}$Indium (III) in the form of the acetate.

The library consists of $^{111}$Indium DO3A-labelled endothelin related peptides.

EXAMPLE 2

Library Synthesis

Synthesis of a library of contrast agents consisting of GdDTPA bisamides:

Diethylenetriamine pentaacetic acid bisanhydride (DTPA-A) is added to a mixture of 40 different primary and secondary amines (in total 2 equivalents relative to DTPA-A, 0.05 equivalents of each amine) in dry chloroform or acetonitrile (depending on the nature of amines). The mixture is refluxed under nitrogen atmosphere for 24 hours. The solvent is evaporated, the residue is dissolved in distilled water and titrated (arsenazo III) with gadolinium chloride solution at pH 4.5–6.

The library contains up to 1560 different GdDTPA-bisamides.

EXAMPLE 3

In Vivo Selection

In vivo selection from a library of radiopharmaceutical contrast agents comprising $^{111}$Indium chelates. Targeting of receptors:

A library of $^{111}$Indium DO3A-labelled endothelin related peptides (Example 1) is injected i.v. into rat tail vein (the rat model relevant for cardiovascular diseases). The biodistribution of the library is followed by scintigraphy. Endothelin (or another known compound with very high affinity for endothelin) is injected i.v. in the same rat after 24 hours. The excreted contrast agents or metabolites thereof are collected from bile and urine from the time of this second injection for 12 hours, purified and analysed with HPLC-MS. The same rat may later be used for similar experiments using other libraries.

A similar experiment can be done with other libraries, like for example a somatastain contrast agent library, and animal tumor models. Similar experiments can also be performed by use of libraries of non-radioactive analogues of radioactive contrast agents; for example by use of nonradioactive isotopes of the same isotope (for example nonradioactive chromium instead of $^{51}$Cr or nonradioactive iodine instead of radioiodine) or by use of nonradioactive isotopes of other elements that have the same biological properties as the radioactive element of interest (bioisosteric).

EXAMPLE 4

In Vivo Selection

In vivo selection from a library of paramagnetic MR contrast agents. Renal and hepatobiliary excretion:

A library of paramagnetic chelates (Example 2) is injected into rat tail vein (normal rat). Bile and urine samples are collected during four hours and the samples collected every 20 minutes are analysed with HPLC-MS.

The result is a good correlation between chemical structure and renal/hepatobiliary excretion.

EXAMPLE 5

Library Synthesis

Preparation of a library of gas-filled microbubbles tagged with radioactive material:

Perfluorobutane containing microbubbles (phosphatidylserine (90 mol %), phosphatidylethanolamine DTPA (5 mol %) (prepared according to Grant et al. in Magn Res. Med 11 236–243 (1989) and Mal-PEG$_{3400}$-DSPE (5 mol %)) are prepared according to Example 2e) in PCT/GB97/02954 published May 7, 1998.

The particles are labelled with $^{111}$In in 3 different concentrations (T1, T2 and T3) (See FIG. 1). Three different ligands (A, B and C) are coupled to the particles followed by pooling and splitting. The 3 particle suspensions are further tagged with different concentrations of $^{153}$Sm (U1, U2 and U3). Three different ligands (A, B, C) are coupled to the particles and the result is 3 libraries each containing 3 ultrasound contrast agents each with a unique radioactive label. This can be expanded to very big libraries using combinations of many different isotopes.

EXAMPLE 6

In Vivo Selection

In vivo selection and identification of tissue-specific ultrasound contrast agents from a library of ultrasound contrast agents tagged with radioisotopes:

A library of ultrasound contrast agents tagged with different radioisotope mixtures (from Example 5) is injected into pigs with arteriosclerosis (established model). The accumulation of contrast agent in the region of interest is followed by gamma camera and the chemical composition of contrast agents of interest is determined by detection of the composition of gamma radiation using a multichannel gamma counter. (Identification of tagging and thereby identification of contrast agent).

What is claimed is:
1. A method of contrast agent drug candidate selection which involves:
(i) obtaining a combinatorial library comprising an admixture of potential contrast agent drug candidates each incorporating a reporter moiety which is detectable in an animate human or non-human animal body, said library comprising a plurality of said reporter moieties which are interdistinguishably detectable in said body,

(ii) administering said library to the animate human or non-human animal body, (iii) identifying in vivo one or more of said reporter moieties having a desired distribution and/or elimination pattern in said body and thereby identifying a member of said library which has said pattern or a sub-set of said library which contains a member of said library which has said pattern.

2. A method as claimed in claim 1 wherein said nonhuman animal body is a mammalian, avian or reptilian body.

3. A method as claimed in claim 1 wherein said reporter moiety is selected from the group consisting of radiolabels, chromophores, tags with different magnetic moments, tags with different paramagnetic centres, and tags with differently sized or membraned gas containing microballoons.

4. A method as claimed in claim 1 wherein a combination of reporter moieties are incorporated into individual members of said combinational library.

5. A method as claimed in claim 1 wherein each different library member incorporates a different reporter moiety or a different combination of reporter moieties and wherein detection of said reporter identifies the library member of which it forms a part.

6. A method as claimed in claim 1 wherein a subset of members of said library incorporates a particular reporter moiety and detection of said reporter identifies a sub-set of the library members that include said reporter.

7. A method as claimed in claim 1 wherein said reporter moieties are interdistinguishably detectable using different imaging techniques.

8. A method as claimed in claim 7 wherein the identification of one or more of said reporter moieties in step (iii) is carried out by imaging the body or site of interest therein using two or more different imaging techniques.

9. A method as claimed in claim 1 wherein said reporter moieties are interdistinguishably detectable using one imaging technique.

10. A method as claimed in claim 9 wherein the identification of one or more of said reporter moieties in step (iii) is carried out by imaging the body or site of interest therein using one imaging technique.

11. A method as claimed in claim 1 comprising the use of at least one combinational library having at least 3 library members.

12. A method as claimed in claim 1 comprising the use of at least one combinational library having at least 100 library members.

13. A method as claimed in claim 1 wherein at least 2 different reporter moieties are present in the said library.

14. A method as claimed in claim 1 wherein at least 25 different reporter moieties are present in the said library.

15. A method as claimed in claim 1 wherein the ratio of library members to different reporters is in the range of 25:1 to 1:1.

16. A method as claimed in claim 15 wherein the ratio of library members to different reporters is 1:1.

17. A method as claimed in claim 1 wherein the in vivo identification is carried out by whole body imaging using an imaging modality to detect said reporter moieties.

18. A method as claimed in claim 1 wherein the library members comprise a first reporter moiety effective as a contrast agent, a tag unique to the member or a set of members and, optionally, a targeting moiety.

19. A method as claimed in claim 1 further comprising the step of manufacturing said contrast agent drug candidate selected or a component or derivative thereof and optionally formulating it with at least one pharmaceutical carrier or excipient.

* * * * *